May 31, 1966 | E. S. BOERNER | Plant Pat. 2,640
CHRYSANTHEMUM PLANT
Filed June 7, 1965
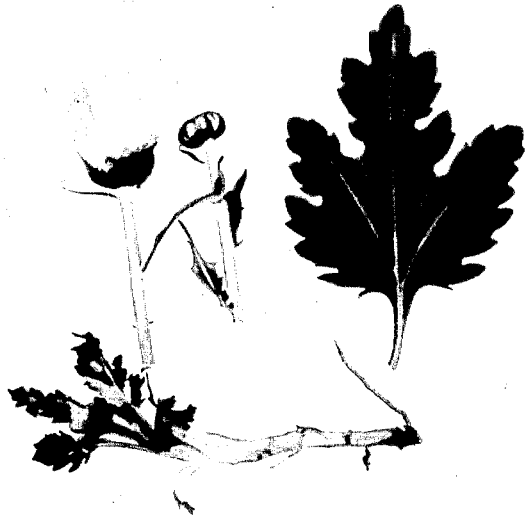
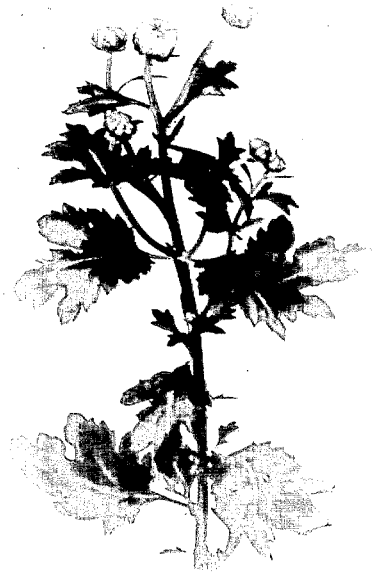
Inventor.
E. S. Boerner
By: Robb & Robb
Attorneys.

United States Patent Office

Plant Pat. 2,640
Patented May 31, 1966

2,640
CHRYSANTHEMUM PLANT

Eugene S. Boerner, Newark, N.Y., assignor to Jackson & Perkins Company, Newark, N.Y., a corporation of New York Filed June 7, 1965, Ser. No. 462,155
1 Claim. (Cl. Plt.—79)

The present invention relates to a new and distinct variety of chrysanthemum plant of the decorative spoon class, which was originated by me by crossing an unnamed and unpatented selfed-seedling of the chrysanthemum variety known as "Swallow" (Plant Patent No. 1,106) with itself.

The primary objective of this breeding was to produce a new and improved chrysanthemum variety having the early blooming habit and strength of the variety "Swallow," but which bears flowers of a different color. This objective was fully achieved along with other desirable improvements, as evidenced by the following unique combination of characteristics which are outstanding in the new variety and distinguish it from its parents, as well as from all other varieties of which I am aware:

(1) An upright, free and strong habit of growth;
(2) An early blooming habit;
(3) Clean foliage which clothes the plant to the ground;
(4) A waxed texture of the flower petals;
(5) A double and spooned flower petal form; and
(6) A distinctive and attractive general color tonality of the flowers corresponding to Orange-Buff, lightly overcast with Deep Chrome.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—An unnamed selfed-seedling of "Swallow."
*Pollen parent.*—Self.
Classification: Decorative spoon.
Growth: 20 inches tall; compact.
Location where observations made: Outdoors at Newark, New York, in the early morning during the early part of the month of October.

Cold resistance: Winter hardy in northern New York State.
Blooming period: From early September until frost.

*Flower*

Bud:
*Color.*—When petals first divide—Coral Red, Plate 13. When petals begin to unfurl—Ochraceous-Salmon, Plate 15. When half-blown: Inside—Orange-Buff, Plate 3, with spoon Flame Scarlet, Plate 2; outside—Ochraceous-Buff, Plate 15. Plate 15.
*Peduncle.*—Color—Kildare Green, Plate 31. Strength—strong.
Bloom:
*Size.*—5½ inches in diameter.
*Stem.*—Strong.
*Form.*—Decorative spoon.
*Petalage.*—Very double when fully opened; spooned.
*Color.*—Center of flower—Salmon-Orange, Plate 2, very lightly overcast with Orange-Buff, Plate 3. Outer petals—Orange-Buff, Plate 3, lightly overcast with Light Orange-Yellow, Plate 3. Base of petals—Barium Yellow, Plate 16. Inside of petal—Orange-Buff, Plate 3, lightly overcast with Deep Chrome, Plate 3. Reverse of petals—Capucine Buff, Plate 3.
*Petals.*—Texture—waxed. Form.—spooned.
*Fragrance.*—Characteristic chrysanthemum.

*Plant*

Form: Upright.
Growth: Free.
Foliage:
*Size.*—Medium; foliage extends to the ground.
*Quantity.*—Normal.
*Color.*—Upper side—Deep Dull Yellow-Green (1), Plate 32. Reverse side—Light Bice Green, Plate 17.
*Texture.*—Leathery; clean.

I claim:

A new and distinct variety of chrysanthemum plant of the decorative spoon class, substantially as herein shown and described, characterized particularly as to novelty by the unique combination of an upright, free and strong habit of growth, an early blooming habit, clean foliage which clothes the plant to the ground, a waxed texture of the flower petals, a double and spooned flower petal form, and a distinctive and attractive general color tonality of the flowers corresponding to Orange-Buff, lightly overcast with Deep Chrome.

No references cited.

ABRAHAM G. STONE, *Primary Examiner.*